(12) United States Patent
Malek et al.

(10) Patent No.: US 8,781,194 B2
(45) Date of Patent: Jul. 15, 2014

(54) ANEURYSM DETECTION

(75) Inventors: Adel M. Malek, Lexington, MA (US);
Eric Miller, Newton, MA (US);
Alexandra Lauric, Medford, MA (US)

(73) Assignee: Tufts Medical Center, Inc., Boston, MA (US)

( * ) Notice: Subject to any disclaimer, the term of this patent is extended or adjusted under 35 U.S.C. 154(b) by 829 days.

(21) Appl. No.: 12/761,936

(22) Filed: Apr. 16, 2010

(65) Prior Publication Data

US 2010/0284587 A1 Nov. 11, 2010

Related U.S. Application Data

(60) Provisional application No. 61/170,281, filed on Apr. 17, 2009.

(51) Int. Cl.
*A61B 1/002* (2006.01)
*A61B 1/005* (2006.01)

(52) U.S. Cl.
USPC .......................... 382/131; 382/128; 382/154

(58) Field of Classification Search
USPC .......................... 382/128, 131, 154
See application file for complete search history.

(56) References Cited

U.S. PATENT DOCUMENTS

| | | | |
|---|---|---|---|
| 5,924,997 A * | 7/1999 | Campbell | 600/549 |
| 6,047,090 A | 4/2000 | Makram-Ebeid | |
| 6,377,832 B1 | 4/2002 | Bergman et al. | |
| 8,170,304 B2 * | 5/2012 | Tek et al. | 382/128 |
| 8,170,307 B2 * | 5/2012 | Karmonik et al. | 382/128 |
| 2002/0065542 A1 * | 5/2002 | Lax et al. | 607/99 |
| 2002/0077564 A1 * | 6/2002 | Campbell et al. | 600/549 |
| 2005/0018900 A1 * | 1/2005 | Bruijns | 382/154 |
| 2005/0147297 A1 | 7/2005 | McLaughlin et al. | |
| 2005/0259854 A1 | 11/2005 | Arimura et al. | |
| 2007/0150208 A1 * | 6/2007 | Dewey | 702/27 |
| 2008/0118127 A1 | 5/2008 | Sirohey et al. | |
| 2008/0170763 A1 * | 7/2008 | Begelman et al. | 382/128 |
| 2008/0249755 A1 | 10/2008 | Tek et al. | |
| 2009/0012430 A1 | 1/2009 | Lovoi et al. | |
| 2009/0088624 A1 | 4/2009 | Nussbaumer | |
| 2009/0214097 A1 | 8/2009 | Mohamed et al. | |
| 2009/0216307 A1 * | 8/2009 | Kaufmann et al. | 623/1.3 |
| 2009/0238420 A1 * | 9/2009 | Rongen et al. | 382/128 |

FOREIGN PATENT DOCUMENTS

JP 2004201873 A * 7/2004
JP 2011004923 A * 1/2011

OTHER PUBLICATIONS

Y. Uchiyama et al. "Computer Aided Diagnosis Scheme for Detection of Unruptured Intracranial Aneurysms in MR Angiography". Proceedings of the 2005 IEEE. Engineering in Medicine and Biology 27th Annual Conference. Shanghai, China, Sep. 2005. pp. 3031-3034.

(Continued)

*Primary Examiner* — Hiep V Nguyen
*Assistant Examiner* — Teresa Woods
(74) *Attorney, Agent, or Firm* — Occhiuti & Rohlicek LLP

(57) ABSTRACT

An approach to automatically detecting, classifying and/or highlighting abnormal structures such as brain aneurysms is based on three-dimensional studies of the brain vessels. The approach is applicable to effectively all currently available modalities of acquisition of the cerebral vessels, including magnetic resonance angiography (MRA), computed tomography angiography (CTA), and conventional catheter-based three-dimensional rotational angiography (3DRA).

50 Claims, 8 Drawing Sheets

(56) References Cited

OTHER PUBLICATIONS

Figure 1:
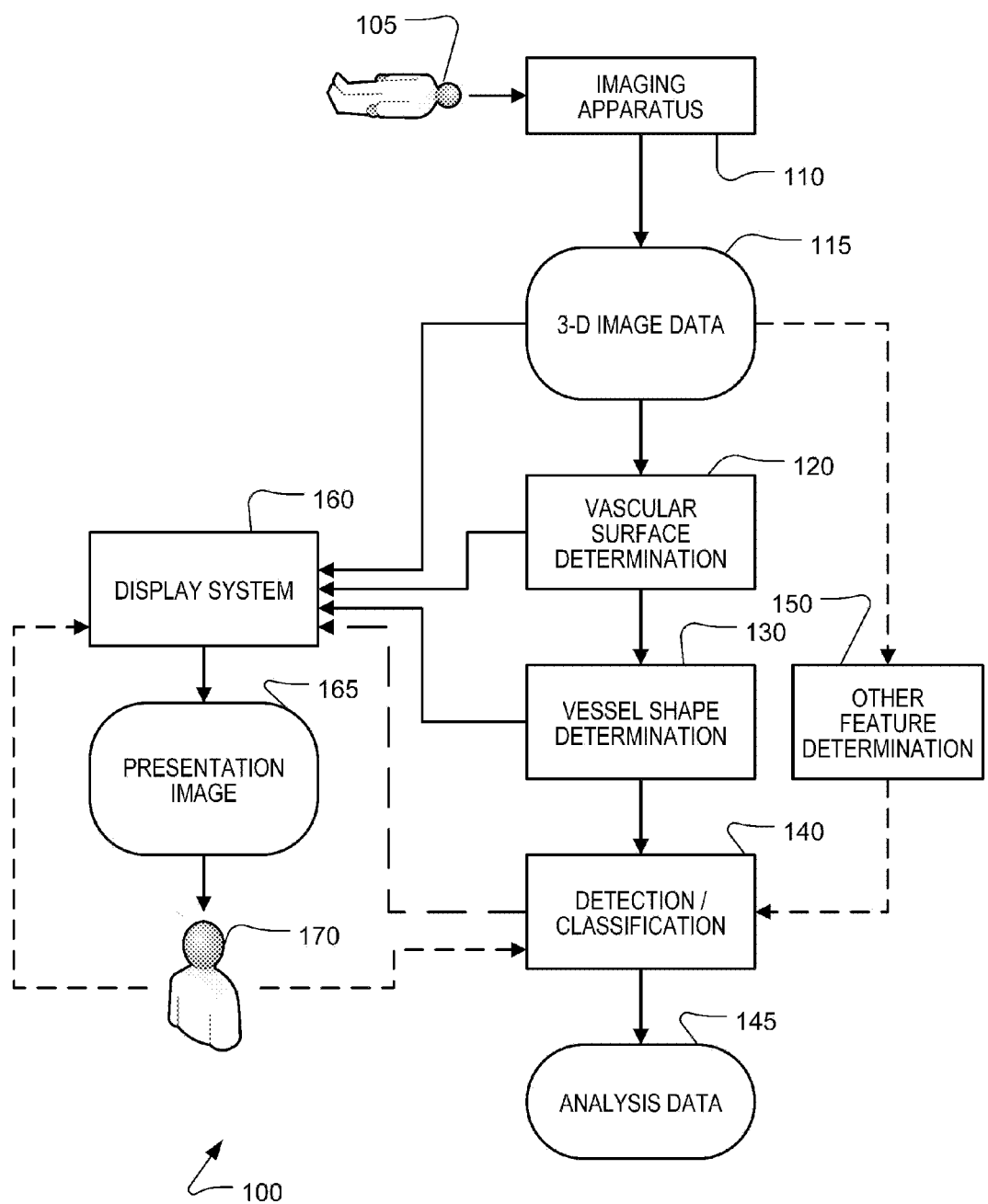

Arimura et al. "Automated Computerized Scheme for Detection of Unruptured Intracranial Aneurysms in Three-Dimensional Magnetic Resonance Angiography." Academic Radiology, vol. 11, No. 10, Oct. 2004. pp. 1093-1104.

Arimura et al. "CAD Scheme for Detection of Intracranial Aneurysms in MRA based on 3D Analysis of Vessel Skeletons and Enhanced Aneurysms." Medical Imaging, 2005. Proceedings of SPIR—the international society of optical engineering. pp. 967-974.

Arimura et al. "Computerized detection of intracranial aneurysms for three-dimensional MR angiography: Feature extraction of small protrusions based on a shape-based difference image technique." Medical Physics, vol. 33, No. 2, Feb. 2006. pp. 394-401.

Kobashi et al. "Computer-Aided Diagnosis of Intracranial Aneurysms in MRA Images with Case-Based Reasoning." The Institute of Electronics, Information and Communication Engineers, vol. E89-D, No. 1, Jan. 2006. pp. 340-350.

Hoh et al. "Bottleneck Factor and Height-width Ratio: Association with Ruptured Aneurysms in Patients with Multiple Cerebral Aneurysms." www.neurosurgery.online.com vol. 61, No. 4, Oct. 2007. pp. 716-723.

Raghavan et al. "Quantified aneurysm shape and rupture risk". J. Neurosurg. vol. 102, Feb. 2005. pp. 355-362.

Dhar et al. "Morphology Parameters for Intracranial Aneurysm Rupture Risk Assessment." www.neurosurgery-online.com vol. 63, No. 2, Aug. 2008. pp. 185-197.

\* cited by examiner

| Threshold value (region index) | TPF (%/100) | FN (avrg per study) | FP (avrg per study) |
|---|---|---|---|
| 0 | 1 | 0 | 3.66 |
| 5 | 1 | 0 | 1.33 |
| 7.5 | 1 | 0 | 1 |
| 10 | 1 | 0 | 0.66 |
| 12.5 | 0.87 | 0.11 | 0.44 |
| 15 | 0.50 | 0.33 | 0.22 |
| 17.5 | 0.35 | 0.33 | 0.22 |

| Threshold value (region index) | TPF (%/100) | FN (avrg per study) | FP (avrg per study) |
|---|---|---|---|
| 0 | 1 | 0 | 28.80 |
| 5 | 1 | 0 | 5.36 |
| 7.5 | 0.90 | 0.10 | 3.27 |
| 10 | 0.81 | 0.18 | 2.27 |
| 12.5 | 0.81 | 0.18 | 1.54 |
| 15 | 0.81 | 0.18 | 1.36 |
| 17.5 | 0.63 | 0.36 | 1 |

| Type  | N   | Features | Accuracy % |
|-------|-----|----------|------------|
| SW+BF | 117 | AR       | 60.3       |
| SW+BF | 117 | Size     | 57.8       |
| SW+BF | 117 | AR, Size | 62.6       |
| SW    | 58  | AR       | 69.2       |
| SW    | 58  | Size     | 70.6       |
| SW    | 58  | AR, Size | 72.2       |
| BF    | 59  | AR       | 61.5       |
| BF    | 59  | Size     | 46.7       |
| BF    | 59  | AR, Size | 60.2       |

FIG. 8A

| Type | N | Aneurysm Model (AM) | Parent Vessel Model (PVM) | Best Features AM | Best Features PVM | Accuracy % |
|---|---|---|---|---|---|---|
| SW+BF | 117 | X | | $\mu_2, \mu_3, \mu_4, \mu_5, h$ | | 67.9 |
| SW+BF | 117 | | X | | $\mu_2, \mu_7, \mu_8, k_4, h$ | 68.3 |
| SW+BF | 117 | X | X | $\mu_2, \mu_3, \mu_5$ | $\mu_8, h$ | 64.3 |
| SW | 58 | X | | $\mu_2, \mu_3, \mu_8, k_5, h$ | | 81.2 |
| SW | 58 | | X | | $\mu_4, \mu_6, \mu_7, \mu_8, h$ | 72.2 |
| SW | 58 | X | X | $\mu_2, \mu_3, \mu_8$ | $k_5, h$ | 86.7 |
| BF | 59 | X | | $\mu_2, \mu_3, k_4, k_5, h$ | | 60.3 |
| BF | 59 | | X | | $\mu_3, \mu_4, \mu_8, k_5, h$ | 71.2 |
| BF | 59 | X | X | | $\mu_3, \mu_4, \mu_8, k_5, h$ | 71.2 |

FIG. 8B

ANEURYSM DETECTION

CROSS-REFERENCE TO RELATED APPLICATIONS

This application claims the benefit of U.S. Provisional Application No. 61/170,281, titled "Aneurysm Detection," filed on Apr. 17, 2009, which is incorporated herein by reference.

BACKGROUND

This document relates to detection of vascular abnormalities, for example, detection of brain aneurysms.

Computer-aided systems have been proposed for locating possible aneurysm areas from an image of a vasculature volume, for example, to assist diagnosticians with their interpretations and to reduce diagnostic times. In general, prior detection schemes are dependent on the imaging modality, for example, because both the segmentation of the vessels and the false positive reduction use image characteristics.

The detection of brain aneurysms plays a key role in reducing the incidence of intracranial subarachnoid hemorrhage (SAH) which carries a high rate of morbidity and mortality. The majority of non-traumatic SAH cases are caused by ruptured intracranial aneurysms and accurate detection can decrease a significant proportion of misdiagnosed cases. Subarachnoid hemorrhage (SAH) is a serious cause of stroke which affects 30,000 patients in North America annually. SAH accounts for a quarter of cerebrovascular deaths, with 80% of the non-traumatic SAH cases being caused by a ruptured intracranial aneurysm. An intracranial aneurysm is a localized pathological dilatation of a blood vessel. It is reported that up to 2% of the general population harbors aneurysms. Most of these aneurysms are asymptomatic and remain undetected with only a small proportion proceeding to rupture and consequent SAH, with an annual incidence of approximately 1%. However, in the case of a ruptured aneurysm, the initial bleed is fatal in 10-20% of instances and despite improvements in patient management, the incidence of SAH has not declined over time and the morbidity rate is still reported between 25% and 50% in patients surviving aneurysm ruptures.

Detecting intracranial aneurysms from imaging scans is an important step in the prevention of aneurysmal SAH and its attendant complications, as treatment of aneurysms using endovascular or surgical methods carries a lower rate of complication when performed in unruptured versus ruptured aneurysms. Although aneurysm detection is currently performed visually by experienced diagnosticians, there is an increasing interest in computed-aided diagnostic (CAD) systems to assist diagnosticians and possibly improve diagnostic accuracy, while limiting missed detection.

Recent advancements in imaging technologies and the increasing use of less invasive computed tomography (CT) and magnetic resonance imaging (MRI) in outpatient settings, has led to an increased detection of incidental, asymptomatic unruptured intracranial aneurysms (UIA) during the routine evaluation of headache, dizziness, and trauma. While, with rare exceptions, the recommendation is for all unruptured symptomatic aneurysms to be treated, the management of asymptomatic UIA remains controversial. Recent studies estimate the annual rupture rate at only 0.1-0.2%, in contrast with earlier data which reported an annual rupture rate of 1-2%. Since preventive treatment carries risks of complications which increase with age, the decision to intervene and treat UIA needs to be balanced against the risk of rupture. To this end, the International Study of Unruptured Intracranial Aneurysms (ISUIA) released the conclusions of two studies in 1998 and 2003 with the goal of defining an optimal treatment management of UIA. The size and location of the aneurysms were concluded to play important roles in predicting rupture risk and a threshold of 7 mm diameter was proposed.

Under the influence of ISUIA studies, the largest diameter of the aneurysm is a commonly used index to predict rupture. However, it is well known that many small aneurysms rupture, whereas other large aneurysms never do. The aspect ratio (aneurysm height/neck width) is another popular size index used to predict the risk of rupture, especially for small aneurysms which might be missed by the largest diameter measure. A threshold value of 1.6 was recommended for the aspect ratio (AR) to discriminate between unruptured and ruptured aneurysms. While proving useful in many cases, there are studies which report finding no statistically significant difference in AR between ruptured and unruptured aneurysms or dispute how to best use the measure.

Cerebral aneurysms have various shapes and sizes and like size, shape is likely to have an impact on the rupture risk. With advances in medical imaging, modalities such as 3D rotational angiography (3D-RA), computed tomography angiography (CTA) and magnetic resonance angiography (MRA) can capture the complexity of the volumetric shape and offer the possibility to analyze aneurysms in a 3D environment. Still, the morphological characterization of brain aneurysms is an open research area.

SUMMARY

In one aspect, in general, intracranial aneurysms are automatically detected. Applied to the segmented cerebral vasculature, the method detects aneurysms as suspect regions on the vascular tree, and is designed to assist diagnosticians with their interpretations and thus reduce missed detections. In some examples of the approach, the vessels are segmented and their medial axis is computed. Small regions along the vessels are inspected and the Writhe Number is introduced as a new surface descriptor to quantify how closely any given region approximates a tubular structure. Aneurysms are detected as non-tubular regions of the vascular tree.

In another aspect, in general, an approach is directed to automatically detecting and/or highlighting abnormal structures such as brain aneurysms based on three-dimensional studies of the brain vessels. The approach is applicable to effectively all modalities of acquisition of the cerebral vessels, including magnetic resonance angiography (MRA), computed tomography angiography (CTA), and conventional catheter-based three-dimensional rotational angiography (3DRA).

In another aspect, a medical imaging system is augmented with a computer implemented method for enhancing presentation images formed by the system by automatically detecting and/or classifying vascular abnormalities using local measures of vessel surface shape, for instance, according to distributions of such measures, and providing visual indications of such detections and/or classifications in the presentation images.

In another aspect, in general, a method for analysis of a vascular system includes accepting data characterizing a surface structure of a vascular system of a subject. The data identifies locations on the surface of vessels of the vascular system. At each of the identified locations of the surface of the vessels, a local descriptor of vessel shape is determined.

Aspects can include one or more of the following features.

The local descriptor of vessel shape is determined based on a local neighborhood of the vessel surface.

Determining the local descriptor of vessel shape includes determining the neighborhood to include the identified location and extending along the direction of blood flow of the vessel.

The extent of the neighborhood in the direction of blood flow of the vessel includes at least a length of vessel greater than a diameter of the vessel in a vicinity of the identified location.

The local descriptor of vessel shape at the identified location comprises an accumulation over locations in the neighborhood of pairwise geometric relationships of the surface at the identified location and at the location in the neighborhood.

The determined local descriptors of vessel surface shape are used to determine diagnostic information for presentation.

Determining the local descriptor of vessel shape comprises determining a set a neighboring locations on the surface of the vessel. For each neighboring location, a quantitative relationship between the identified location and the neighboring location is determined, and the determined quantitative relationships are combined to form the local descriptor of shape. In some examples, determining a set of neighboring locations depends on an estimated radius of the vessel at the identified location.

Determining the quantitative relationship between the identified location and the neighboring location comprises combining directions of a normal to the vessel surface at each of the identified location and the neighboring location. In some examples, determining the quantitative relationship between the identified location and the neighboring location further comprises combining the directions of the normal to the vessel surface and a direction between the identified location and the neighboring location. In some examples, combining the determined quantitative relationships comprises summing the determined quantitative relationships.

The diagnostic information characterizes a degree of abnormality of the vessel surface shape.

The diagnostic information characterizes a classification of an abnormality of the vessel surface.

The diagnostic information comprises a classification of a region of the vascular system based on a distribution (e.g., a statistical distribution) of the local descriptor of vessel surface shape. For instance, the classification of the region comprises a classification of an aneurysm according to a rupture criterion.

Determining the diagnostic information comprises detecting regions of the vascular system according to the determined local descriptors of vessel surface shape. For instance, detecting regions of the vascular system comprises detecting aneurysms.

Distributional characteristic of the local descriptor of vessel shape are computed over a region of the vessel surface, and the computed distributional characteristic are used in a classification of the region of the vessel surface The method further includes identifying the locations on the surface of vessels, segmenting a three-dimensional image of a body including the vascular system to identify regions of the vascular system in the image, and identifying locations on boundaries of the identified regions.

The method further includes acquiring the three-dimensional image of the body.

The method further includes presenting a display of the determined descriptors of vessel shape as a view of a three-dimensional image associating the determined descriptors and their corresponding locations. For instance, presenting the display further comprises highlighting display of a three-dimensional image of a body.

Determining the local descriptor of vessel shape comprises determining a quantity indicative of a degree of abnormality.

Determining the local descriptor of vessel shape comprises determining a quantity indicative of a degree of symmetry of the vessel surface.

Determining the local descriptor of vessel shape comprises determining a quantity indicative of a degree of similarity of the vessel shape upstream and downstream along the direction of blood flow at the point.

Determining the local descriptor of vessel shape comprises computing a Writhe Number.

In another aspect, in general, classification of an aneurysm, for example, according to a class defined by a rupture characteristics (e.g., ruptured versus unruptured), makes use of an analysis that includes characteristics of the vessel both at the site of the aneurysm as well as on the parent vessel. In some examples, this analysis includes computing distributional characteristics at surface points on a neighborhood that includes both the aneurysm and the parent vessel (e.g., including an upstream as well as a downstream portion of the parent vessel). In some examples, this analysis includes computing characteristics based on one or more geometric relationships between the aneurysm and the parent vessel. An example of such a geometric relationship includes an angle of the aneurysm (e.g., angle between a principal axis of the aneurysm and a medial axis of the parent vessel, the inflow angle of the aneurysm, or the angle separating the parent vessel and the aneurysm dome main axis).

In another aspect, in general, software stored on a computer-readable medium includes instructions for causing a data processing system to accept data characterizing a surface structure of a vascular system, the data identifying locations on the surface of vessels of the vascular system; and at each of the identified locations of the surface of the vessels, determine a local descriptor of vessel shape, wherein the descriptor characterizes a degree of abnormality of the vessel shape.

In some examples, a population based statistics, for instance based on a population-based atlas, provide a range of expected values of the descriptor of these in normal patients or in patients with various disease states.

In another aspect, in general, a system for analysis of a vascular system includes an input module for accepting data characterizing a surface structure of a vascular system, the data identifying locations on the surface of vessels of the vascular system, and an analysis module configured to, at each of the identified locations of the surface of the vessels, determine a local descriptor of vessel shape, wherein the descriptor characterizes a degree of abnormality of the vessel shape.

In another aspect, in general, a method is adapted to classification of regions of a vascular system. Data characterizing a surface structure of a vascular system of a subject is accepted (e.g., from an imaging system). The data identifies locations (e.g., voxels in an image) on the surface of vessels of the vascular system. Data identifying a specified portion of the vascular system is also accepted. In some examples, these portions are identified based on a manual examination of an image of the vascular system, while in other examples, these portions are identified using an automated detection approach. A region of the surface structure associated with the specified portion is determined, and one or more features are computed at points of the determined region. A distributional characteristic of the one or more of computed features are computed, and a classification of the specified portion is formed according to the computed distributional characteristics.

Aspects may include one or more of the following.

Determining the region of the surface structure comprises forming a region extending along the direction of blood flow of the vessel.

Determining the region of the surface structure comprises forming a region protruding on a sidewall of the vessel.

Computing the one or more features includes computing a Writhe Number.

Computing the one or more features includes computing a curvature. For instance, a mean curvature or a Gaussian curvature is computed at points of the determined region.

Computing the distributional characteristics includes computing at least one of a percentile, a moment, and a cumulant of a distribution.

Corming the classification includes classifying an identified aneurysm according to a rupture characteristic.

Classifying the aneurysm includes applying a statistical classification adapted to at least one of a bifurcation class and a sidewall class of aneurysms.

Advantages of one or more aspects can include one or more of the following.

Use of the Writhe Number computed on a neighborhood of surface locations (e.g., voxels) without requiring first modeling or surface fitting provides a more direct measurement of surface characteristics and thereby can preserve more information about the surface shape for use in detection or classification tasks. For example, fitting a circle or ellipse to a cross-sectional area or a cylinder to a section of vessel may not be most effective when the vessel deviates from that class of shapes.

Use of a descriptor of vessel shape, which considers an entire section of vessel extending in the direction of bloodflow (e.g., plus and minus one radius upstream and downstream on the vessel), provides a descriptor that can provide greater information than a local descriptor of surface shape, such as local curvature or cross-sectional radius. For instance, detection of vessel shape abnormalities may require further processing of estimated radius or non-circular cross-section over a range of points along the vessel, whereas at least some of the approaches described herein directly provide a descriptor of vessel shape without requiring such post-processing.

Large amounts of data can be processed to detect aneurysmal dilatations with a high degree of accuracy. The sensitivity of this method is of great value to the physician (radiologist, neurologist, or neurosurgeon) trying to detect vascular lesions that may be otherwise missed on visual inspection as is currently the common practice.

The approach can serve as a supplemental computer-aid to currently existing imaging systems to improve the detection of potentially fatal cerebral aneurysms.

Aspects of the approach are not necessarily limited to a particular imaging modality. This generality can provide an advantage because, in addition to MRA, several other modalities are used for cerebral vasculature imaging aneurysm detection, such as catheter-based digital subtraction angiography (DSA) and associated 3DRA, as well as CTA. Therefore, independence of the approach from imaging modality is a desirable feature in any aneurysm detection method. In some embodiments, a segmented volume of the cerebral vasculature is used as input and the segmentation is generally dependent on the imaging acquisition system. However, the actual detection approach is independent of the imaging modality and can be designed as a third party application.

In initial studies, the approach was very sensitive (close to 100%) and returned very few false positive results without needing a complex false positive reduction scheme. Both saccular aneurysms (generated by dilating an artery in one direction perpendicular to the vessel axis) and fusiform aneurysms (generated by dilating the entire artery segment in more than one direction perpendicular to the vessel axis) are successfully detected.

The approach does not require forming a model of the vessels, for example, as cylinders or circular cross-section tubes.

The approach does not require a library of predefined shapes or parameters known to represent potential aneurysms.

Other features and advantages of the invention are apparent from the following description, and from the claims.

DRAWINGS

Figure 2A:
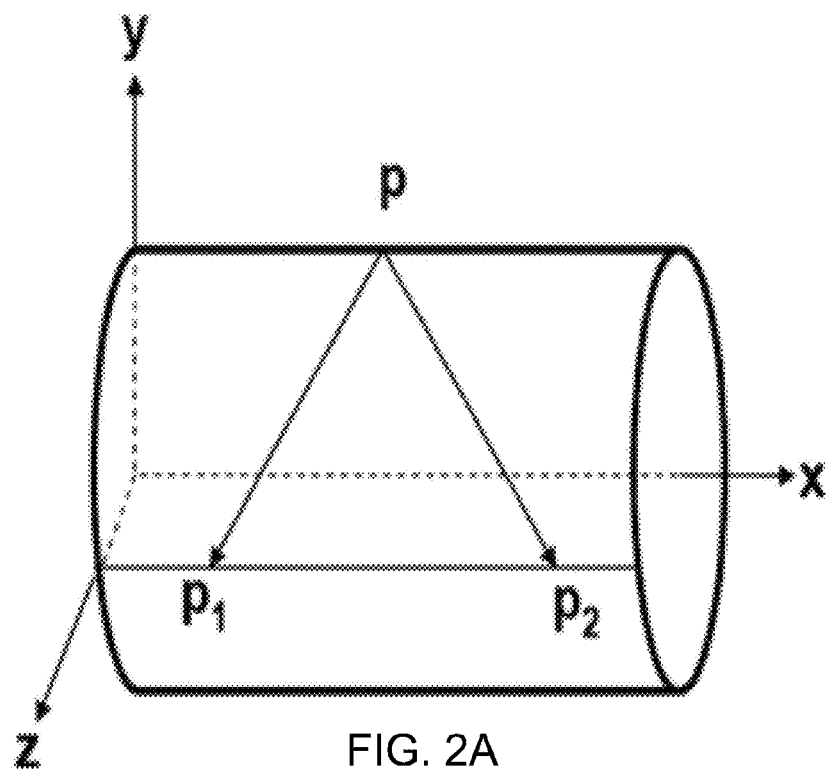
Figure 2B:
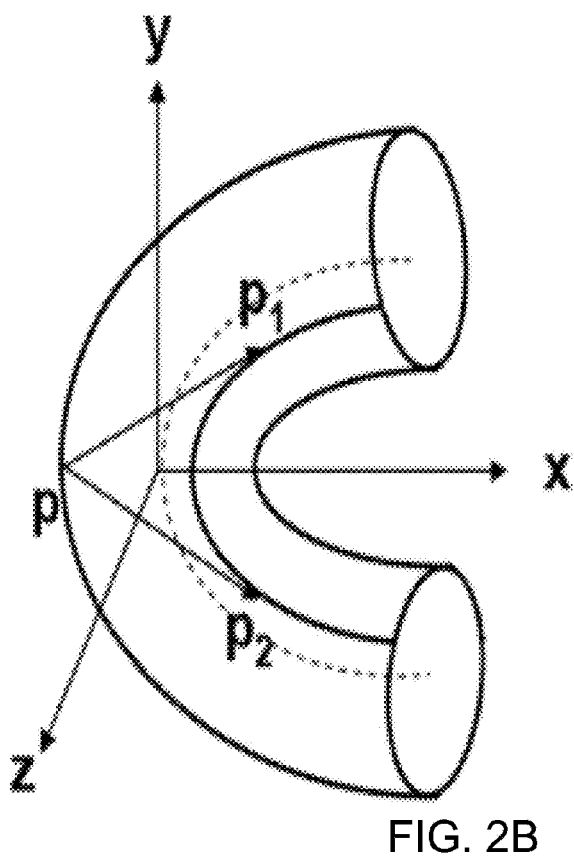
Figure 3A:
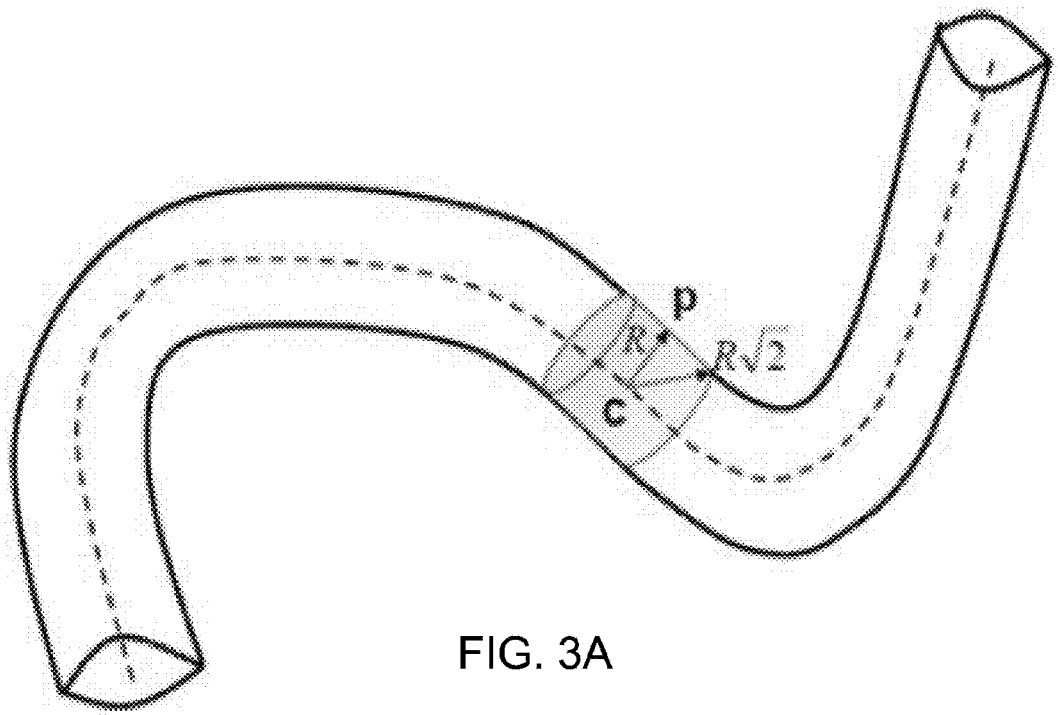
Figure 3B:
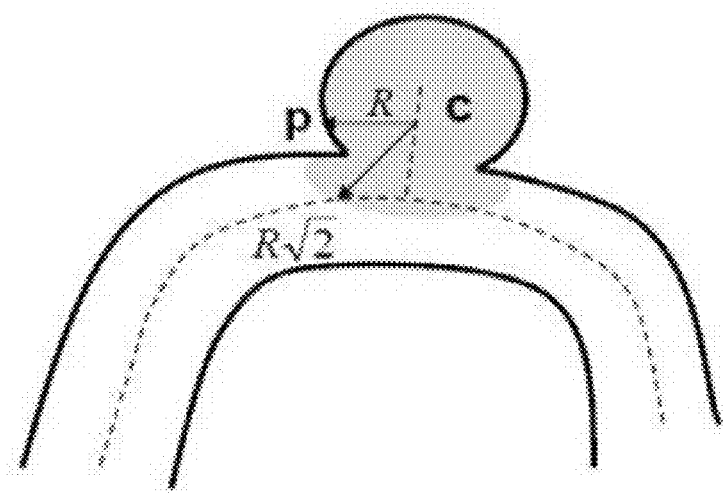
Figures 4A, 4B, 5:
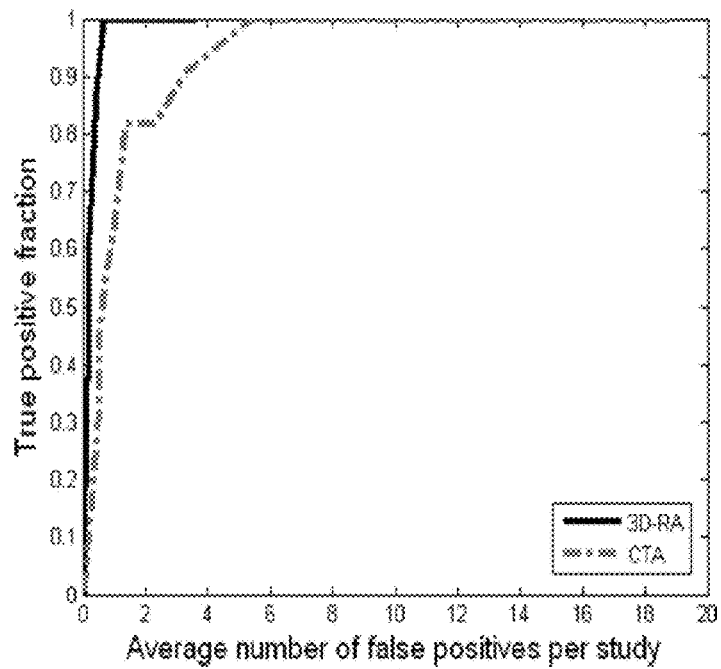
Figure 6A:
Figure 6B:
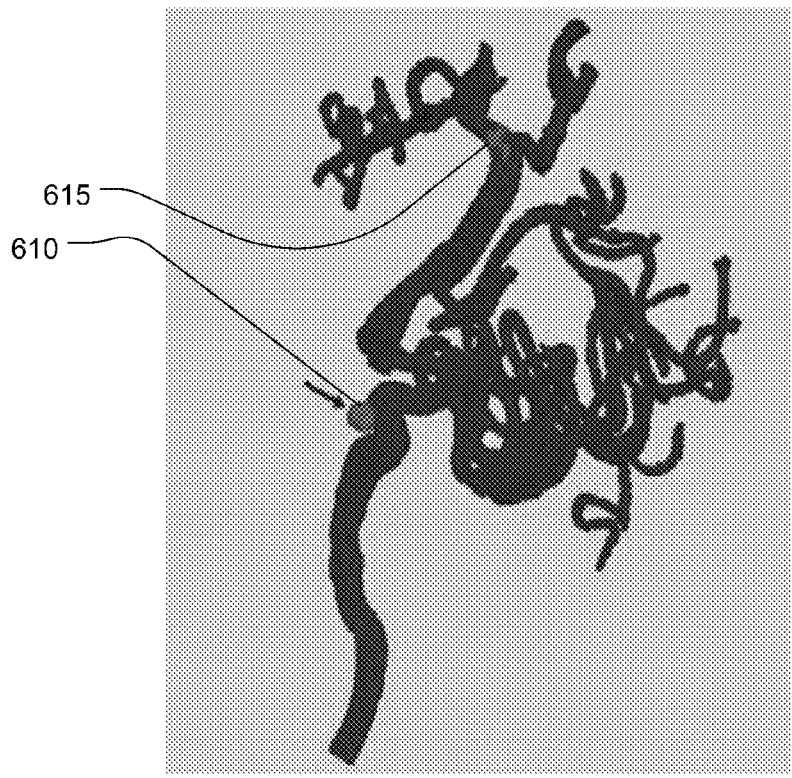
Figure 7A:
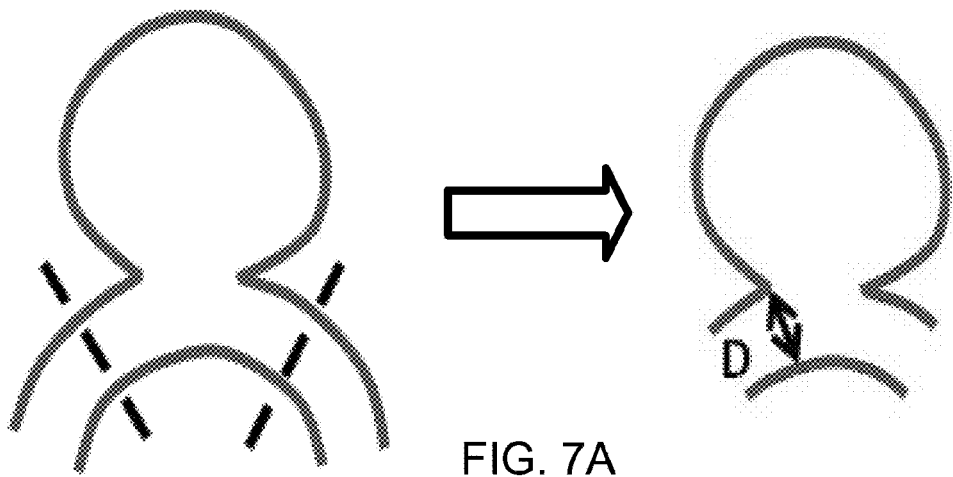
Figure 7B:
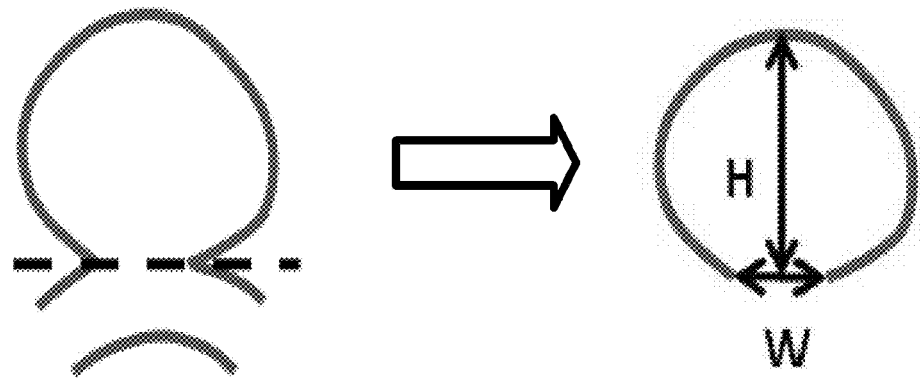

FIG. 1 is a block diagram of a system for vascular analysis;

FIGS. 2A-B are schematic diagrams of cylindrical and parabolic vessel sections;

FIGS. 3A-B are diagrams illustrating specification of local neighborhoods of surface points;

FIGS. 4A-B are tables of detection results;

FIG. 5 is a plot of a Free Response Operating Characteristic (FROC);

FIGS. 6A-B are examples of enhanced images showing automatically detected aneurysms;

FIGS. 7A-B are schematic diagrams of selection of aneurysm surfaces for classification; and FIG. 8A is a table of classification results using size and aspect ratio, and FIG. 8B is a table of classification results using features representing local measures of vessel shape.

DESCRIPTION

1 Overview

Several approaches to detection, visualization, classification, or other automated analyses of vascular abnormalities based on three-dimensional images of patients are described below. Particular examples of these approaches are applied to brain aneurysms. One feature of a number of these approaches is the use of a local measure (descriptor) of vessel shape, without necessarily requiring the fitting of models, such as circular cross-sections, to conduct an analysis. In particular, one local measure of vessel shape described below, which is evaluated at a point on the vessel, depends of the shape of the vessel over a range that extends upstream and downstream along the direction of bloodflow as opposed to considering only a cross section of the vessel. Such a local measure of vessel shape does not necessarily require further processing to identify abnormalities based on variation along the direction of bloodflow because of its inherent consideration of variation over the extended range along the vessel in the computation of the measure.

In some examples, distributional characteristics of surface, cross-sectional, and/or extended vessel space characteristics, for instance, characteristics of distributions of local measures of vessel shape, are used in discrimination or classification approaches.

Some embodiments of a system 100, which is used to analysis and/or display of vascular information for a patient 105, include some or all of the components shown in the FIG. 1. An imaging apparatus 110, for example, a Computed Tomography (CT) or Magnetic Resonance (MR) angiography apparatus, is used to produce three-dimensional image data 115 for the patient. In some examples, this data is in the form of a series of cross-sectional data sets. This data is represented, for instance through a process of resampling or other form of image processing, for further processing as an image volume partitioned into an arrangement of three-dimensional voxels, for example forming cubic volumes with 0.48 mm sides.

Generally, a vascular surface determination process 120 involves first segmenting the image volume into voxels that are part of the vascular system and those that are not. In some examples, this segmentation step uses prior art techniques, which are generally dependent on the underlying imaging modality. Based on the segmentation, and generally independent of the underlying image or the modality of the image acquisition, a set of voxels are identified as being on the surface of vessels. In some examples, the surface voxels are determined to be voxels that are segmented to be vascular voxels, with at least one non-vascular adjacent voxel. Also based on the volume segmentation, voxels on the medial axes of the vessels are determined. In some examples, a skeletonization algorithm is used to determine the medial axes.

A vessel shape determination process 130 is used to analyze the structure of the determined vessel surface. In some examples, a local measure of vessel surface shape is computed for some of all or the surface voxels. In some examples, the degree of abnormality is based on the locations of other nearby (i.e., in a defined neighborhood) surface voxels. In some examples, this neighborhood is defined to extend upstream and/or downstream from the location, for example, extending approximately one radius value upstream and one radius value upstream from the location. In some examples, the neighborhood extends both along the direction of blood-flow, as well as extending around the entire cross-section of the vessel, for instance, with the neighborhood forming a tubular section. In some examples, the quantity represents a degree of symmetry of the vessel surface, or to a degree of similarity of the vessel shape "upstream" and "downstream" of the point. This measure may be an indicator of possible aneurysm in the vicinity of the analyzed voxel location.

In the system shown in FIG. 1, a display system 160 is used to produce a presentation image 165 for presentation to a clinician 170. For instance, the presentation image shows the results of the vessel shape determination process as a view of a three-dimensional image. In some examples, an originally acquired image is enhanced to indicate locations of high degrees of abnormality.

In some examples, the quantities computed to represent vessel shape are passed to a detection or classification procedure 140. For example, the procedure discriminates between ruptured and unruptured aneurysms. The results of such classification may be passed to the display system 160, for example, to indicate different classes of detected aneurysms in different ways (e.g., different colors), or to limit highlighting of aneurysms of a particular class (e.g., ruptured). In some examples the classification procedure 140 produces analysis data 145, which may be applied to further processing or display steps.

2 Writhe Number

As discussed further below, in some examples, a local measure of vessel shape is applies a computation based on or motivated by a computation of the Writhe Number of a surface. The Writhe Number has been applied in curve theory to measure how much a curve twists and coils around itself. In biomedical engineering, the two-dimensional Writhe Number has been used to study the shape and topology of DNA, or to characterize the shape of curves, such as the curves of sulci and gyri on the cortical surface.

As used in this specification a Writhe of surfaces is defined to be similar to that of the Writhe of curves, except using surface normals rather than curve tangents. Given two points p and p' on a surface S, we define a relationship w between them as $$w(p, p') = \frac{[\hat{n}_p, p' - p, \hat{n}'_p]}{\|\hat{n}_p\| \cdot \|p' - p\| \cdot \|\hat{n}'_p\|},$$

where $\hat{n}_p$ is the surface normal at point p, $\| \|$ is the norm of a vector and [a, b, c] is the triple scalar product of vectors a, b and c. The triple scalar product is defined as $$[a,b,c] = a \cdot (b \times c)$$

where $a \cdot b$ denotes a dot product and $b \times c$ denotes a cross product. The absolute value of the triple scalar product is the volume of the parallelepiped defined by vectors a, b and c. The quantity w(p,p') is a pseudoscalar, meaning that it behaves like a scalar but changes sign under inversion.

An example of a local descriptor of shape of a vessel surface at a point p uses neighborhood N(p) of other surface points p' as follows:

$$W(p, N(p)) = \int_{p' \in N(p)} w(p, p') dp'$$

which is discretized as a sum over a neighborhood of voxels $$W(p, N(p)) = \sum_{p' \in N(p)} w(p, p')$$

Note that the neighborhood is can have different definitions in different examples. As discussed below, in some examples, the neighborhood extends for a distance along the blood vessel, being formed by cutting the vessel perpendicularly to its axis. In other examples, the neighborhood does not include closed cross-sections of the vessel, for example, being restricted to a section formed intersecting a cutting plane with the vessel where the cutting plane is not perpendicular to the vessel axes (e.g., selected to cut a sidewall aneurysm from the vessel). Other examples of a neighborhood N(p) of a point p may be defined based on a sphere or other geometric shape centered or referenced to the point, for example, selecting the points within the extent of the shape as the neighborhood. Furthermore, in some examples, the integral or sum is weighted, for example, based on a distance between p and p'.

Referring to FIGS. 2A-B, for certain geometries of the neighborhood N(p), the descriptor W(p,N(p)), can be shown to be zero. For instance, referring to FIG. 2A, if N(p) is a cylinder that extends an equal distance in each direction from a surface point p, for every point $p_1 \in N(p)$ there exists a second point $p_2 \in N(p)$, such that the Euclidean distance $\|p_1 - \| = \|p_2 - p\|$ and the line segment $p_1 p_2$ lies on the cylinder surface. Effectively, such pairs of points $p_1, p_2$ cancel each others in the Writhe Number summation and therefore W(p,N(p)) is zero. Referring to FIG. 2B, a similar cancellation for pairs of points $p_1, p_2$ occurs when N(p) is a non-self-intersecting extruded parabola, its medial axis is a parabola, again resulting in a zero measure. The shapes shown in FIGS. 2A-B are not necessarily exhaustive of shapes that have zero or small Writhe Number.

Very generally, when the local surface deviates from the characteristics such as those shown in FIGS. 2A and 2B, the measure is positive, which in some examples is used as a measure of abnormality of the local surface shape.

3 Detection Example

In a first example, a system 100 is used for detection of aneurysms, for example, to present an enhanced image 165 to a clinician 170 as illustrated in FIG. 1, with locations on the vessel structure highlighted to indicate possible abnormalities at those locations. As introduced above, the detection method takes as input 3D image data 115 in which the cerebral vasculature has been segmented from the background. The medial axis of the vessels is computed from the segmented volume. We consider that aneurysms appear as short branches in the medial axis of the vasculature. Local neighborhoods are determined for surface points along short branches. The Writhe Numbers, as defined above, are computed for each local neighborhood and regions with nonzero Writhe Numbers (or Writhe Numbers exceeding a selected threshold, possibly selected by the clinician) are reported (e.g., displayed to the clinician) as possible aneurysms. In some examples, the size of each region is determined and small regions are eliminated from results based on a thresholding criteria.

The detection method uses a segmented volume of the cerebral vasculature. The appropriate segmentation method depends on the modality of the input data (CTA, MRA, 3D-RA). The medial axis of the vessels is computed, for example, applying the method described by Bouix et al. (2005) and using a skeletonization algorithm which exploits the distance field corresponding to the segmented vessels.

This example of an aneurysm detection method takes advantage of the fact that aneurysms often appear as small branches along the medial axis. Once the medial axis is computed, each voxel on the medial axis is labeled as an end point (the voxel has one adjacent neighbor), a connecting point (the voxel has two adjacent neighbors) or a junction point (the voxel has three or more adjacent neighbors). Short branches are paths between end points and junction points having the length smaller than a threshold value where the threshold is set using voxel dimensions to detect aneurysms up to 50 mm long. In studies, 90% of the aneurysms are smaller than 25 mm in diameter and only 10% are giant aneurysms with sizes between 25-50 mm (Rooij and Sluzewski, 2006). It should be noted that most of the short branches determined this way are actually noise on the medial axis and are only few voxels long. However, in this example, the medial axis provides useful information about aneurysms locations and while reducing the sensitivity of the medial axis algorithm or smoothing the result might reduce the number of short branches, it could also result in misdetection of small aneurysms.

In some examples, the local neighborhoods are determined for the collection of points on the surface of short branches. Given a surface point, p, we want to determine its local neighborhood N(p). A second point, c, is found such that c belongs to the medial axis, c is the closest point to p and c was labeled as a short branch medial point. In most of the cases, p is a point on the surface of normal vessels and c is a noise point on the medial axis sitting close to the true medial axis of the region, as illustrated in FIG. 3A.

Let R be the Euclidean distance between points c and p. The local neighborhood of point p is built around point c and is defined as the connected set of points whose Euclidean distance is within $R\sqrt{2}$ from c (FIG. 3A). Using this method, the local neighborhood of p is a small segment of the vasculature. In the case of a cylinder, the $R\sqrt{2}$ threshold guarantees a one-to-one length-diameter aspect ratio, which works well in practice. Depending on the local bending of the vessels near p, the medial axis of N(p) can be approximated by either a line segment and in this case c is the midpoint of the segment, or by a parabola in which case c is the apex of the parabola. For healthy vessels, the construction guarantees that p sits on a mirror plane of N(p).

The local neighborhood of a surface point is determined as described above independent of the location of the point on the vasculature. FIG. 3B shows the local neighborhood of a point on the surface of an aneurysm. The neighborhood contains part of the aneurysm as well as a portion of the parent vessel. Because the points on the surface of an aneurysm concentrate around the same medial axis points, they share the same local neighborhood. Even in those cases where the aneurysm area might display some symmetries, most surface points will not sit on mirror planes and will have non-zero Writhe Numbers. Exceptions might be fusiform aneurysms which present as local dilatations of an artery, having perfectly circular cross-sections and showing symmetries similar to those of normal vessels. In practice, the method is able to detect certain biological fusiform aneurysms because of their uneven dilatations in multiple directions perpendicular to the vessel axis.

For each local neighborhood, the Writhe Numbers are computed as specified above. To a very high degree of accuracy, the nominal behavior of the vasculature results in the Writhe Number being equal to zero for the neighborhoods along healthy vessels. This follows because locally normal vessels are shaped as cylinders or extruded parabolas which in theory have a zero Writhe Number. The local neighborhoods of points on the aneurysms do not display the same symmetries as cylinders and extruded parabolas and as a result have non-zero Writhe Numbers.

Adjacent voxels on the surface of the vessels having non-zero Writhe Numbers are clustered in regions which are considered positive results and are highlighted as possible aneurysms. The detection method based on Writhe Numbers shows high specificity and as a result we are able to threshold positive results using simple features related to the size of the candidate regions. Specifically, in some experiments, our source data originated from multiple modalities, collected with different scanner models, and having different voxel sizes, therefore, the number of voxels within each positive region is a poor indicator of the absolute physical size of the region. The size of a voxel plays a significant role in discriminating between true positives and false positive based on region size, since the same number of image voxels describe different physical sizes depending on the resolution of the data. For instance, an image region of 100 voxels describe a larger physical region on a dataset with voxel size 0.5×0.5× 1.00 mm$^3$ than is does on a dataset with voxel size 0.5×0.5× 0.5 mm$^3$.

In order to analyze positive regions in a unique manner across modalities and scanners, we define a region index as the product between the size of the region in voxels and the volume of the voxel. We effectively add the volume of all voxels on the surface of the positive region. We use the region index as an alternative to the surface area of the positive regions in order to avoid the triangulation of the surface. Under this definition, 100 voxels describe a region index of 25 on a dataset with voxel size 0.5×0.5×1.00 mm$^3$. The same 100 voxels describe a region index of 12.5 on a dataset with voxel size 0.5×0.5×0.5 mm$^3$. The region index gives an intuition of the physical size of a positive result independent of the resolution of the input data. True positives tend to have a larger region index than false positives and in this work we threshold positive results based on their region index. We show below how detection and false positive statistics change according to the threshold value of the region index.

In alternative approaches to processing the values computed at individual locations, rather than or in addition to using a spatial extent based filtering approach, distributional information of the values may be used. For example, characteristics of a distribution of the value over a range, for example, within a spatial range of the point (for example, define in a manner similar to the definition of the neighborhood) can be used, and characteristics of the distribution (e.g., mean, median, perceptual, moments, cumulants, etc,) may be used to filter the values for use in detection or image enhancement.

This aneurysm detection method was tested on ten distinct 3DRA and ten unrelated CTA patient-derived datasets. The twenty datasets contain twenty aneurysms, with one study showing no aneurysms and one study having two aneurysms. The aneurysms have diameters in the range 3.2-10.2 mm and lengths in the range 3.5-13 mm. Among the aneurysms, six are sidewall aneurysms (dilation of the artery in one direction perpendicular to the vessel axis), nine are bifurcation aneurysms (dilation at the bifurcation of arteries) and five are fusiform aneurysms (dilation of the artery in multiple directions more or less perpendicular to the vessel axis). All aneurysms were identified a priori and classified by two independent operators.

The 3D rotational angiography (3D-RA) data were acquired using a biplane flat-detector digital subtraction angiography system (Axiom Artis, Siemens Medical Solutions, Malvern, Pa.) at Tufts Medical Center, Department of Neurosurgery (Boston, Mass.). 3D-RA is a technique employed to visualize blood vessels in a bony or dense soft tissue environment. Contrast agent is injected through a catheter which is navigated from a percutaneous femoral arterial access into a carotid or vertebral artery (i.e. one of the vessels leading to the brain vasculature). Images acquired during the contrast agent are subtracted from images acquired pre-contrast. In the case of intracranial scanning, 3D-RA produces images with very high contrast between vasculature and the surrounding environment (FIG. 3a). In the current study, the size of each 3D-RA data volume is 256×256×229, with 0.48 mm isotropic voxels.

To visualize blood vessels, CTA relies on 2D X-ray images acquired in the presence of an iodine-based contrast injected as an intravenous solution. Two scanners were used for the acquisition of the CTA datasets: definition (Siemens Medical Solutions, Malvern Pa.; voxel size 0:35×0:35×1 mm) and LightSpeed Plus (GE Medical Systems, Schenectady N.Y.; voxel size 0:40×0:40×1:25 mm).

Although catheter-based 3D-RA imaging remains a standard in cerebral aneurysm imaging, CTA is a less-invasive modality with increasingly improving sensitivity and specificity, which is being more and more used for cerebrovascular imaging and aneurysm detection.

In some examples, prior to segmenting the vasculature, CTA data volumes were resampled to isotropic voxel size (e.g., to form the 3-D image data 115 in FIG. 1). Because of the high resolution of the data and high contrast between vasculature and surrounding tissue, vessel segmentation of 3D-RA data is a relatively simple task. CTA images have lower spatial resolution compared to 3D-RA and may show physical (partial volume, beam hardening) and patient-related artifacts (metal, motion effects). The contrast agent injected during CTA imaging increases the image contrast between vessels and surrounding soft tissue, but lowers the contrast between vessels and bone, making cerebral vessel segmentation more challenging. Furthermore, CTA data display venous contamination of the images (i.e. contrast agent reaching the venous system and precluding adequate visualization of arteries). In the case of CTA, the bone was removed from the images using a commercial 3D visualization and modeling system (Amira, Mercury Systems, Chelmsford, Mass.). Vessel segmentation was performed on all datasets using a combination of thresholding and region-growing techniques (e.g., Pham et al., 2000 "Current methods in medical image segmentation." *Annual Review of Biomedical Engineering* 2, 315-337.). The resulting segmented volumes were used as input to the aneurysm detection method.

Applying this detection approach, all aneurysms were correctly identified with 0.66 false positives per study on 3D-RA data and 5.36 false positives per study on CTA-derived data. These results were obtained as follows. We start by clustering voxels whose Writhe Number is non-zero and then computing the region index associated with each cluster. Suspect regions are taken as those whose region index exceeds a given threshold. The performance analysis in this paper is evaluated by varying this threshold and examining relevant statistics.

Specifically, for each threshold value, the following quantities were computed: number of true positives (TP), number of false positives (FP), number of false negatives (FN) and true positive fraction (TPF). The true positive fraction is defined as $$TPF = \frac{TP}{TP + FN}$$

The sensitivity of the method is measured in percentage and is computed as TPF×100.

Tables shown in FIGS. 4A-B show how detection statistics change function of the region index threshold value applied on the detection results, for 3D-RA (FIG. 4A) and CTA (FIG. 4B), respectively. It is apparent from the two tables that most false positive results have very small region indexes. The purpose when applying the region index threshold is to reduce the FP value, while maintaining a TPF value of 1. TPF equals 1 when all aneurysms are detected.

The method detected all aneurysms and resulted in 3.66 false positives for 3D-RA data and 28.80 for CTA data. These are detection results before any false positive reduction, which show that the detection specificity is much higher on 3DRA data than on CTA. The first level of thresholding (with a region index of 5) reduces the CTA false positives from 28.80 to 5.36 and the 3D-RA positive results from 3.66 to 1.33, showing that most false positives are very small in size, especially for CTA data. The 3D-RA false positives can be further thresholding for a region index up to 10 which corresponds to 0.66 false positives per study.

To evaluate the performance of the proposed detection method, Free Response Operating Characteristic (FROC) analysis was applied as shown in FIG. 5. The horizontal axis indicates the average number of false positives (FP) per study, while the vertical axis indicates the true positive fraction (TPF), which is related to the sensitivity of the detection. Specifically, the FROC curves were determined by plotting TPF (second column from the tables of FIGS. 4A-B) as a function of FP (fourth column from the tables of FIGS. 4A-B) for both 3D-RA and CTA data. FIG. 5 shows how many false positive results are observed on average before one aneurysm is detected for 3D-RA (0.66 false positives) and CTA (5.36 false positives). The results correspond to thresholding positive results with a region index of 10 and 5 for 3D-RA and CTA, respectively.

Referring to FIGS. 6A-B, examples of presentation images 165 (see FIG. 1) show the visual results of the detection algorithm after thresholding positive results with region index smaller than 10. An automatically detected areas 610 and 615 are highlighted, with areas 610 corresponding to positive results (true aneurysm indicated with the arrows, which are not automatically produced), and areas 615 corresponding to false positives.

As shown by the FROC analysis (see FIG. 5), the detection algorithm performs very well on 3D-RA data and results in few false positive results (0.66 per study). 3D-RA images have high resolution and show high contrast between vasculature and surrounding tissue and simple segmentation techniques result in accurate segmented volumes. Segmentation is more challenging on CTA data which have lower resolution, more artifacts and show venous contamination.

There is a direct relationship between the quality of vessel segmentation and the accuracy of the detection method. Because this study focused on aneurysm detection, simple, readily available segmentation methods were used to preprocess the image data. However, particularly for CTA imaging, it is likely that better segmentation techniques would improve the detection strengths of each imaging modality.

The clinical value of the algorithm depends on its performance on less-invasive CTA and MRA modalities. The current method can be generalized to include non-invasive cross-sectional imaging modalities. The input modality will, in general, affect the choice of optimal segmentation algorithms and the effect of the segmentation performance on the detection results.

The presence of noise in the medial axis calculation, especially for narrow vessels (2-3 voxels in diameter) is likely a reason for a large portion of the false positive results. In some examples, an optional step automatically groups the positive results describing the same aneurysm. This yields larger region indexes for true positives and a more discriminant false positive reduction.

4 Classification Example

In a second example, the classification procedure (block 140, FIG. 1) is applied to predicting whether a cerebral aneurysm has ruptured (e.g, computing the likelihood of representing an aneurysm that has ruptured). As in the detection example described above, the cerebral vasculature is first segmented from the 3D-RA volume. In a number examples of the classification approach described below, distributional characteristics of features of local surface shape (e.g., curvature), cross-sectional shape (e.g., diameter, circularity, aspect ratio), and/or local vessel shape (e.g., Writhe Number, degree of cylinder or sphere shape), are used in the classification approach, with the underlying distributions being defined over a neighborhood of vessel surface.

As described below, in some classification examples, the locations of the aneurysms is given. For instance, a clinician may located the aneurysms manually (e.g., using a presentation image enhanced as described above), or in other examples, the locations of the aneurysms may be automatically detected using the approach described above without manual intervention.

Referring to FIGS. 7A-B, for each aneurysm two separate 3D models are created, one in which the aneurysm is completely separated from the parent vessels (FIG. 7B) and one in which parts of the adjacent vessels are included (FIG. 7A), with the cut being at a distance approximately equal to the diameter (D) of the vessel. These two models are represented as triangular meshes. Writhe numbers are computed along the surface of the models as described above. The Writhe Number distribution for each model is represented as a histogram, which is further approximated to a continuous density function using kernel estimators. Statistics such as central moments, cumulants and entropy are computed for the estimated density function. These shape descriptors are used as classification features in predicting the risk of rupture in cerebral aneurysms. Details about each of these steps are presented below.

For each aneurysm model, the Writhe Number values along the surface are represented in a frequency histogram. The value of each bin is divided by the total number of samples, and the area under the counting bins adds to one. The histogram is a non-smooth estimator of the underlying density function showing discontinuities at its ends and at bins with zero value. Such discontinuities may not reflect the continuous nature of the density function. To avoid these shortcomings, histogram smoothing is performed using kernel estimators.

Kernel smoothing is a technique which results in the approximation of a regression curve (x), by performing a local weighed averaging in a small neighborhood around variable x. The kernel is a continuous, bounded function which integrates to one. The kernel describes the shape of the weight function used in the local approximation. The smoothness of the approximation is controlled by a parameter called bandwidth, which describe the size of the local neighborhood around x. In this work, the approximating function is given by the Nadaraya-Watson estimator with Gaussian kernels.

Statistics such as central moments, cumulants, and entropy are applied to the smoothed histogram to describe and analyze Writhe Number distributions. The central moments of a probability distribution function p(x) are defined as $$\mu_i = \int_{-\infty}^{\infty} (x-c)^i p(x) dx$$

Central moments orders two, three and four have special meaning. The second central moment, $\mu_2$, is the variance and describes the distribution width within the values $x_j$. The third central moments, $\mu_3$, is the skew and characterizes the asymmetry of the shape around the mean. The fourth central moment, $\mu_4$, is the kurtosis and measures the sharpness of the distribution.

The cumulants of a distribution are closely related to the moments of that distribution. The first five cumulants as functions of the central moments are:

$$k_1 = c, k_2 = \mu_2, k_3 = \mu_3, k_4 = \mu_4 - 2\mu_2^2, \text{ and } k_5 = \mu_5 - 10\mu_3\mu_2$$

The fourth order cumulant gives a measure of the non-Gaussianity of the variable x. Distributions with sharp peeks and heavy tails have positive $k_4$, whereas distributions with fatter shapes have negative $k_4$. Gaussian distributions have $k_4 = 0$.

The entropy of a continuous random variable x, with density p(x), is a measure of the uncertainty associated with that variable and it is defined as $$h(x) = -\int_x p(x) \log p(x) dx$$

The entropy does not depend on the values of x and only on the probabilities that x will occur.

In this example, each aneurysm model is described by 10 attributes related to the Writhe Number distribution: central moments orders 2 to 8, cumulants orders 4 and 5, and the entropy of the distribution. Consequently, each natural aneurysm is associated with 20 attributes, 10 describing the aneurysm sac and 10 describing the aneurysm with portion of the parent vessels attached. These descriptors are used as classification features in predicting the likelihood of rupture in cerebral aneurysms.

The classification problem solved here involves 2 classes (ruptured vs. unruptured) and 117 samples (the aneurysms), described by 20 features each. The method used is logistic regression with 10-fold cross validation. The classification is repeated 10 times with 10 different random seeds. This results in 100 different splittings and the average performance is reported.

Classification is first performed on all 117 samples, then separately on 58 sidewall aneurysms and 59 bifurcation aneurysms. In each of these cases, first the aneurysm sac attributes are considered, then only the attributes from aneurysm with parent vessels attached are considered, and finally the total of 20 attributes are considered.

The rupture prediction results using the Writhe Number as described above are compared with those using the aspect ratio index (AR) and the largest diameter size. The table shown if FIG. 8A shows the accuracy for rupture prediction when the aspect ratio and the largest diameter size are considered on the whole set of 117 aneurysms (SW+BF) and on subsets of sidewall (SW) and bifurcation (BF) aneurysms respectively. Both AR and size indexes perform much better on sidewall (72.2% accuracy) vs. bifurcation aneurysms (61.5% accuracy).

The table shown in FIG. 8B summarizes the main results of this study. Classification is performed on the three subsets: 117 SW+BF, 58 SW, and 59 BF aneurysms. For each subset, rupture is predicted by considering first only aneurysm model (AM) features, second considering only parent vessel model (PVM) features, and third considering both AM and PVM features.

The set of features taken into account for each particular classification case are marked in FIG. 8B with an X in the corresponding columns of the table. We distinguish between the features which are taken into consideration, and those which are used for classification. As such, sequential backward selection is applied on the features taken into consideration to reduce the set to the five most significant features, which are the features used for classification.

Best prediction results are obtained when the classification is performed separately on sidewall and bifurcation aneurysms, respectively. The accuracy obtained using morphological analysis based on Writhe Number is of 86.7% for sidewall aneurysms and of 71.2% for bifurcation aneurysms. The results represent an approximately 20% increase in prediction accuracy for both subtypes, compared to when aspect ratio index was considered. Adding parent vessel information increased the prediction accuracy for sidewall aneurysms and proved essential for bifurcation aneurysms.

In terms of features, the entropy is part of all best features sets and it seems to be a significant quantity for both subtypes. The mean entropy is significantly smaller for unruptured vs. ruptured aneurysms. Also, all best feature sets contain at least two of the variance, skewness and kurtosis central moments.

Other detection examples make use of combinations of features, for example, using size, aspect ratio, undulation index, ellipticity index, nonspericity index, and aneurysm to size ratio (e.g., computed in block 150, FIG. 1), in addition to features derived from local measures of surface shape, such as Writhe Number.

In some examples, additional classification features are based on one or more geometric relationships between the aneurysm and the parent vessel. An example of such a geometric relationship includes an angle of the aneurysm (e.g., angle between a principal axis of the aneurysm and a medial axis of the parent vessel, the inflow angle of the aneurysm, or the angle separating the parent vessel and the aneurysm dome main axis). In some examples, additional classification features are based on computational fluid dynamics analysis (e.g., wall shear stress) that depends on the combined shape of the parent vessel and the aneurysm.

Other features of the local measures can be used than those described above. For example, percentile values (e.g., $10^{th}$, $50^{th}$, or $90^{th}$ percentile), and other transformations of distributions (e.g., cosine transform) can be used. Also, non-parametric techniques can be used for classification based on distributions of the local measures, for example, based on nearest neighbor and clustering techniques (e.g., using cross entropy for comparing distributions). Distributions of other local measures can also be used in the classification approaches. For instance, measures such as curvature and diameter can be used.

In some examples, rather than solely training classifier parameters on known training data, parameters may be adapted based on unknown image data, or based on partial manual annotation of an image, to better match the statistics of the unknown image.

As introduced above, it can be useful to used different models for different types of aneurysms. For example, sidewall aneurysms exhibit significantly different statistics than bifurcation aneurysms, and therefore, it is useful to have separate statistical models for these two types. In some examples, these types are identified manually. In other examples, an automated classification of the aneurysm type is used to select the model or model parameters that are appropriate. In some examples, an unsupervised clustering is used to enable modeling of different aneurysm types without requiring manual classification. For example, the distributional characteristics are assumed to come for a set of two (or more generally K) different populations each with a different parametric characterization.

In some examples, rather than characterizing distributional characteristics parametrically, non-parametric techniques are used. For example a distance metric between pairs of sample distributions (histograms), for example, based on cross-entropy of squared error computations, can be used to define distance metrics between training samples of different classes (e.g., normal vessel, ruptured aneurysm, and unruptured aneurysm), and classification can be performed without any model fitting whatsoever.

5 Alternatives

In other embodiments, different definitions of neighborhoods and different quantities representing local shape are used. In some embodiments, combinations of relationships w(p,p') is performed in a weighted manner over a region. In some embodiments, the quantity is computed to be insensitive to the vessel size (for example, by dividing by $R\sqrt{2}$).

Although described in the context of detecting, enhancing, or classifying vascular abnormalities, the approaches described above may be used in the context of other classes of abnormalities. For example, distributional characteristics within defined neighborhoods may be used to classify surface abnormalities of other organs. In other examples, boundary characteristics of objects detected in three-dimensional images, for instance, tumors, may be classified by distributional characteristics of local surface descriptors.

Although many embodiments determine the vascular abnormalities independently of the imaging modality or modalities, other embodiments may take advantage of specific aspects of the modalities used. For example, different modalities may exhibit different statistical characteristics of the computed descriptors of surface and/or vessel shape, and therefore may be treated differently depending on the modality used.

Certain analyses described above make use of determined medial axes of the blood vessels. The analysis may be adapted to avoid such determination, for example, by determining surface normal vectors according to the surface shape rather than direction from the medial axis.

Embodiments described above do not require forming a model of the vessel shape (e.g., as a circular cross-section). In other embodiments, modeling or parametric representation of vessel shape may be incorporated into the procedure, for example, in forming the local measure of vessel shape.

6 Implementations

The approach can be implemented in the form of a computer program (e.g., software instructions stored on a computer readable medium for controlling a data processing system) which would be tailored to accept any current available cross-sectional imaging datasets that are output by clinical CT, MR, and angiography units. Once implemented, the method could be tested in a retrospective and prospective fashion. Finally, once validated using additional clinical datasets, it could be commercialized to one of the radiology equipment manufacturers or to imaging companies as part of a licensing agreement. In some implementations, the commercial application would be as an add-on tool to existing software analysis workstations. Alternatively, a commercial entity could be setup which would enable the on-line uploading from a customer of the relevant dataset online where the detection algorithm would process the dataset for a fee. With further validation, this may become eventually standard of care for a confirmatory detection of aneurysms when any cross-sectional study of the cerebral vasculature is obtained.

In some implementations, the approach is incorporated into a system that acquires a three-dimensional image of a patient and provides a representation of the image to an operator of the system, typically a clinician. In some implementations, the approach is hosted separately from the system that acquires the image, for example in a separate image processing module or server that provides image analysis services. In some implementations, the approach is combined with a system that performs volume segmentation, which may combined with or separate from the image acquisition and/or image display systems.

It is to be understood that the foregoing description is intended to illustrate and not to limit the scope of the invention, which is defined by the scope of the appended claims. Other embodiments are within the scope of the following claims.

What is claimed is:

1. A method for analysis of a vascular system comprising:
accepting data characterizing a surface structure of a vascular system of a subject, the data identifying locations on the surface of vessels of the vascular system based on a segmented three-dimensional image of a portion of the subject's body including the vascular system;
at each of the identified locations on the surface of the vessels, determining, using at least one processor, a local descriptor of vessel shape based on a computation of a Writhe Number that is based on a local neighborhood of the vessel surface corresponding to the identified location, based on quantitative relationships between each location of a plurality of locations in the local neighborhood and the identified location; and
using the determined local descriptors of vessel shape relative to a threshold to determine diagnostic information for presentation.

2. The method of claim 1 wherein determining the local descriptor of vessel shape includes determining the local neighborhood to include the identified location and extending along the direction of blood flow of the vessel.

3. The method of claim 1 wherein the extent of the local neighborhood in the direction of blood flow of the vessel includes at least a length of vessel greater than a diameter of the vessel in a vicinity of the identified location.

4. The method of claim 1 wherein the local descriptor of vessel shape at the identified location comprises an accumulation, for each of the plurality of locations in the local neighborhood, of a pairwise geometric relationship between the identified location and the location in the neighborhood.

5. The method of claim 1 wherein determining the local descriptor of vessel shape comprises:
determining a set of neighboring locations on the surface of the vessel as the plurality of locations in the local neighborhood;
for each neighboring location, determining a quantitative relationship between the identified location and the neighboring location; and
combining the determined quantitative relationships to form the local descriptor of vessel shape.

6. The method of claim 5 wherein combining the determined quantitative relationships comprises summing the determined quantitative relationships.

7. The method of claim 5 wherein determining a set of neighboring locations depends on an estimated radius of the vessel at the identified location.

8. The method of claim 5 wherein determining the quantitative relationship between the identified location and the neighboring location comprises combining directions of a normal to the vessel surface at each of the identified location and the neighboring location.

9. The method of claim 8 wherein determining the quantitative relationship between the identified location and the neighboring location further comprises combining the directions of the normal to the vessel surface and a direction between the identified location and the neighboring location.

10. The method of claim 1 wherein the diagnostic information characterizes a degree of abnormality of the vessel shape.

11. The method of claim 1 wherein the diagnostic information characterizes a classification of an abnormality of the vessel shape.

12. The method of claim 1 wherein determining the diagnostic information comprises detecting regions of the vascular system according to the determined local descriptors of vessel shape.

13. The method of claim 12 wherein detecting regions of the vascular system comprises detecting aneurysms.

14. The method of claim 1 further comprising acquiring the three-dimensional image of the body.

15. The method of claim 1 further comprising:
presenting a display of the determined local descriptors of vessel shape as a view of a three-dimensional image associating the determined descriptors and their corresponding locations.

16. The method of claim 15 wherein presenting the display further comprises highlighting display of a three-dimensional image of a body.

17. The method of claim 1 wherein determining the local descriptor of vessel shape comprises determining a quantity indicative of a degree of abnormality.

18. The method of claim 1 wherein determining the local descriptor of vessel shape comprises determining a quantity indicative of a degree symmetry of the vessel shape.

19. The method of claim 1 wherein determining the local descriptor of vessel shape comprises determining a quantity indicative of a degree of similarity of the vessel shape upstream and downstream along the direction of blood flow at the point.

20. The method of claim 1 wherein determining the diagnostic information comprises computing a distributional characteristic of the local descriptor of vessel shape over a region of the vessel surface, and using the computed distributional characteristic in a classification of the region of the vessel surface.

21. The method of claim 20 wherein the region of the vessel surface comprises an aneurysm region, and the classification of the region comprises a classification according to a rupture criterion.

22. The method of claim 1 wherein determining a local descriptor of vessel shape includes computing a curvature.

23. The method of claim 1 wherein prior to using the determined local descriptors to determine diagnostic information for presentation, using the determined local descriptors to detect a vessel abnormality.

24. The method of claim 1, wherein the threshold is zero.

25. Software stored on a non-transitory computer-readable medium comprising instructions for causing a data processing system to:
accepting data characterizing a surface structure of a vascular system of a subject, the data identifying locations on the surface of vessels of the vascular system based on a segmented three-dimensional image of a portion of the subject's body including the vascular system;
at each of the identified locations on the surface of the vessels, determining a local descriptor of vessel shape based on a computation of a Writhe Number that is based on a local neighborhood of the vessel surface corresponding to the identified location, based on quantitative relationships between each location of a plurality of locations in the local neighborhood and the identified location; and
using the determined local descriptors of vessel shape relative to a threshold to determine diagnostic information for presentation.

26. A system for analysis of a vascular system comprising:
an input module for accepting data characterizing a surface structure of a vascular system of a subject, the data identifying locations on the surface of vessels of the vascular system based on a segmented three-dimensional image of a portion of the subject's body including the vascular system; and
an analysis module comprising at least one processor configured to, at each of the identified locations on the surface of the vessels, determine a local descriptor of vessel shape based on a computation of a Writhe Number that is based on a local neighborhood of the vessel surface corresponding to the identified location, based on quantitative relationships between each location of a plurality of locations in the local neighborhood and the identified location, wherein the descriptor relative to a threshold characterizes a degree of abnormality of the vessel shape.

27. A method for classification of regions of a vascular system comprising:
accepting data characterizing a surface structure of a vascular system of a subject, the data identifying locations on the surface of vessels of the vascular system based on a segmented three-dimensional image of a portion of the subject's body including the vascular system;
accepting data identifying a specified portion of the vascular system;
determining a region of the surface structure associated with the specified portion;
computing, using at least one processor, a plurality of features at respective points of the determined region, including computing a Writhe Number;
computing distributional characteristics of the computed features, wherein the distribution characteristic is based at least in part on a frequency histogram of values associated with the descriptor of vessel shape;
forming a classification of the specified portion according to the computed distributional characteristics relative to a threshold.

28. The method of claim 27 wherein determining the region of the surface structure comprises forming a region extending along the direction of blood flow of the vessel.

29. The method of claim 27 wherein determining the region of the surface structure comprises forming a region protruding on a sidewall of the vessel.

30. The method of claim 27 wherein computing the plurality of features includes computing a curvature.

31. The method of claim 27 wherein computing the distributional characteristics includes computing at least one of a percentile, a moment, a cumulant, and an entropy of a distribution.

32. The method of claim 27 wherein forming the classification includes classifying an identified aneurysm according to a rupture characteristic.

33. The method of claim 32 wherein classifying the aneurysm includes applying a statistical classification adapted to at least one of a bifurcation class and a sidewall class of aneurysms.

34. A method for analysis of a vascular system comprising:
accepting data characterizing a surface structure of a vascular system of a subject, the data identifying locations on the surface of vessels of the vascular system based on a segmented three-dimensional image of a portion of the subject's body including the vascular system;
at each of the identified locations of the surface of the vessels, determining, using at least one processor, a descriptor of vessel shape based on a three-dimensional model of the vessel surface, wherein the descriptor of vessel shape at the identified location comprises a computed Writhe Number that is insensitive to the size of the vessel in proximity to the identified location; and
using the determined descriptors of vessel surface shape relative to a threshold to determine diagnostic information for presentation.

35. The method of claim 34 wherein the diagnostic information characterizes a degree of abnormality of the vessel surface shape.

36. The method of claim 34 wherein the diagnostic information characterizes a classification of an abnormality of the vessel surface.

37. The method of claim 34 wherein determining the diagnostic information comprises detecting regions of the vascular system according to the determined descriptors of vessel surface shape.

38. The method of claim 37 wherein detecting regions of the vascular system comprises detecting aneurysms.

39. The method of claim 34 further comprising acquiring the three-dimensional image of the body.

40. The method of claim 34 further comprising:
presenting a display of the determined descriptors of vessel shape as a view of a three-dimensional image associating the determined descriptors and their corresponding locations.

41. The method of claim 40 wherein presenting the display further comprises highlighting display of a three-dimensional image of a body.

42. The method of claim 34 wherein determining the diagnostic information comprises computing a distributional characteristic of the descriptor of vessel shape over a region of the vessel surface, and using the computed distributional characteristic in a classification of the region of the vessel surface.

43. The method of claim 42 wherein the region of the vessel surface comprises an aneurysm region, and the classification of the region comprises a classification according to a rupture criterion.

44. The method of claim 42 wherein the distributional characteristic is based at least in part on a frequency histogram of values associated with the descriptor of vessel shape.

45. The method of claim 44 wherein the distributional characteristic comprises an entropy of the frequency histogram.

46. The method of claim 34 wherein the descriptor of vessel shape at the identified location comprises a value based on pairwise geometric relationships over locations in the three-dimensional model of the vessel surface in proximity to the identified location.

47. The method of claim 46 wherein at least one point of each of the pairwise geometric relationships is on the surface of the vessel.

48. The method of claim 46 wherein both points of each of the pairwise geometric relationships are on the surface of the vessel.

49. Software stored on a non-transitory computer-readable medium comprising instructions for causing a data processing system to:
accepting data characterizing a surface structure of a vascular system of a subject, the data identifying locations on the surface of vessels of the vascular system based on a segmented three-dimensional image of a portion of the subject's body including the vascular system;
at each of the identified locations of the surface of the vessels, determining a descriptor of vessel shape based on a three-dimensional model of the vessel surface, wherein the descriptor of vessel shape at the identified location comprises a computed Writhe Number that is insensitive to the size of the vessel in proximity to the identified location; and
using the determined descriptors of vessel surface shape relative to a threshold to determine diagnostic information for presentation.

50. A system for analysis of a vascular system comprising:
an input module for accepting data characterizing a surface structure of a vascular system, the data identifying locations on the surface of vessels of the vascular system based on a segmented three-dimensional image of a portion of the subject's body including the vascular system; and
an analysis module comprising at least one processor configured to, at each of the identified locations of the surface of the vessels, determine a descriptor of vessel shape based on a three-dimensional model of the vessel surface, wherein the descriptor of vessel shape at the identified location comprises a computed Writhe Number that is insensitive to the size of the vessel in proximity to the identified location, wherein the descriptor relative to a threshold characterizes a degree of abnormality of the vessel shape.

\* \* \* \* \*